United States Patent [19]
Lane et al.

[11] Patent Number: 5,605,531
[45] Date of Patent: Feb. 25, 1997

[54] APPARATUS FOR USE WITH ENDOSCOPY AND FLUOROSCOPY FOR AUTOMATIC SWITCHING BETWEEN VIDEO MODES

[75] Inventors: Timothy G. Lane, Merritt Island; Mark J. Weber, Satellite Beach, both of Fla.

[73] Assignee: Tilane Corporation, Rockledge, Fla.

[21] Appl. No.: 225,142

[22] Filed: Apr. 8, 1994

[51] Int. Cl.$^6$ .............................. A61B 1/04; G01N 23/04
[52] U.S. Cl. ...................... 600/118; 600/101; 600/126; 128/653.1; 348/74; 378/63; 378/116
[58] Field of Search ...................................... 128/4–6, 665; 348/65, 74; 378/48, 98, 98.3, 98.5, 63, 114–117; 600/118, 160, 101, 126

[56] References Cited

U.S. PATENT DOCUMENTS

| | | | |
|---|---|---|---|
| 4,821,117 | 4/1989 | Sekiguchi | 128/665 X |
| 4,993,404 | 2/1991 | Lane . | |
| 5,029,016 | 7/1991 | Hiyama et al. | 128/6 X |
| 5,101,272 | 3/1992 | Plut et al. | 378/98.5 X |
| 5,127,394 | 7/1992 | Lane | 128/4 |

*Primary Examiner*—Richard J. Apley
*Assistant Examiner*—John P. Leubecker
*Attorney, Agent, or Firm*—Jones & Askew

[57] ABSTRACT

An apparatus is disclosed for use with a video fluoroscope generating a video output signal in NTSC video format and a video endoscope generating a video output signal in RGB video format. The two video output signals are input into a photo archiving computer video component for archiving and storing still video images on a suitable storage medium. The photo archiving computer is capable of operating in either RGB mode, in which it is capable of processing video signals in RGB video format, or in NTSC video mode, in which it is capable of processing video signals in NTSC video format. The photo archiving computer has a keyboard associated with it and is responsive to a predetermined keyboard sequence for selecting from between RGB and NTSC video modes for operation. However, to eliminate the requirement that the physician press keys on a keyboard when switching between the fluoroscope and the endoscope, the present invention includes a means responsive to operation of the footswitch which actuates the X-ray generator of the fluoroscope to send a signal to the photo archiving computer corresponding to the predetermined keyboard sequence to select NTSC video mode for operation when the fluoroscope footswitch is actuated. When the fluoroscope footswitch is released, the means sends a second signal to the photo archiving computer corresponding to the predetermined keyboard sequence to reselect RGB video mode for operation.

17 Claims, 8 Drawing Sheets

APPARATUS FOR USE WITH ENDOSCOPY AND FLUOROSCOPY FOR AUTOMATIC SWITCHING BETWEEN VIDEO MODES

TECHNICAL FIELD

The present invention relates generally to medical imaging apparatus, and relates more specifically to an apparatus for use with endoscopy and fluoroscopy for automatic switching between video modes.

BACKGROUND OF THE INVENTION

Endoscopes have long been widely used in medical procedures for directly visualizing the interior of a canal or body cavity. A recent improvement on the endoscope is the video endoscope, wherein fiber optics permit the endoscopic view to be displayed on a video monitor. Video endoscopy provides a number of advantages over traditional endoscopy, including permitting more than one person at a time to observe the endoscopic view, permitting the physician to assume a more comfortable viewing angle, and permitting a still photograph and/or videotape record to be made of the endoscopic procedure.

Similarly, modern fluoroscopic technology presents advances over conventional radiography. In conventional radiography, X-rays are projected through a patient onto a photographic film which, when processed, will provide a fixed image of the patient's internal structure In fluoroscopy, the X-ray sensitive photographic film is replaced by a fluorescent screen which, when subjected to X-radiation, produces a direct image of the object under investigation. Because the image on the fluorescent screen is usually so hint that it is difficult to visualize with the unaided eye, the screen image is usually photographed with a sensitive video camera. The video signal is then processed to increase the brightness of the image, and the image is displayed on a video monitor for viewing by the physician. Fluoroscopy affords two primary advantages over conventional radiography: first, the image produced is direct, so there is no need for photographic processing; and second, the image is viewed in "real time", rather than as a still photograph or series of still photographs, and can thus show movement.

Surgical modalities are well known wherein video endoscopy is used in conjunction with dye-injection studies under fluoroscopy at various times during the procedure. Examples of such procedures include endoscopic management of biliary tract obstruction and endoscopic sphincterotomy. In these procedures, the physician uses an endoscope to maneuver a catheter down the esophagus, through the stomach, and into position within either the bile duct or pancreatic duct. The endoscopic view is projected on a first video monitor. A quantity of radiographically opaque dye is then injected through the catheter retrograde into the selected duct. Subsequently, the duct is viewed fluoroscopically on a second video monitor, and the X-rays illuminate the dye to reveal obstructions in the biliary system. If the dye does not properly fill the duct, the catheter may have to be repositioned under endoscopic supervision to permit further infusion of dye. When further dye has been infused, the physician again views the duct fluoroscopically. After the procedure has been completed within the first duct, the physician uses the endoscope to reposition the catheter within the other of the bile or pancreatic duct, and the dye injection procedure is repeated. The physician then looks back to the fluoroscope monitor to visualize the second duct. Depending upon the success of the initial dye injection into the second duct, the physician may again have to redirect his attention to the endoscope monitor to reposition the catheter within the second duct, and then look back to the fluoroscope monitor to view the duct.

U.S. Pat. Nos. 4,993,404 and 5,127,394 disclose apparatus which simplifies this procedure somewhat by providing a control unit which displays both the endoscopic view and the fluoroscopic view on a single monitor. By depressing the foot pedal the physician can toggle back and forth between the endoscopic view and the fluoroscopic view. In addition, the control unit interfaces with the foot pedal which actuates the X-ray generator of the fluoroscope to ensure that the X-ray generator is enabled only when the fluoroscope view is being displayed on the monitor and is disabled when the endoscope view is selected for viewing on the monitor. This feature ensures that the X-ray generator will not be left on accidentally and thus prevents the possibility of the patient and medical personnel being exposed to unnecessary levels of X-rays.

Apparatus for performing medical procedures involving endoscopy and video fluoroscopy are further complicated by the need to record the procedure for future reference. Such recording can typically take any or all of three forms: videotape, still photographs, or magnetic recording and storage of still images for later display. A typical arrangement for endoscopy and video fluoroscopy incorporating recording and storage of images for later display is shown in FIG. 1. A video fluoroscope includes an X-ray generator actuated by a foot pedal. Video outputs from the video fluoroscope and an endoscope are fed into a photo archiving computer, that is, a component which stores and archives still video images on magnetic disk. An example of a photo archiving computer is the Image Manager, marketed by Olympus Corp. A keyboard is associated with the photo archiving computer for entering data, such as the name of the patient, etc. The photo archiving computer can output the endoscope video signal to a video tape recorder (not shown) and also to a still photograph unit (also not shown), which provides a "hard copy" of the endoscope video image at a particular instant. The endoscope video signal is then passed through the still photograph unit to a video monitor, which displays the endoscope video signal for viewing by the physician.

This arrangement is complicated by the fact that the fluoroscope video signal is in NTSC format, while the video endoscope, which can output a video signal in either NTSC or RGB video format, provides best resolution when operating in RGB mode. When the photo archiving computer is operating in RGB mode to receive the signal from the video endoscope, it cannot properly process the NTSC video signal from the video fluoroscope. Conversely when the photo archiving computer is operating in NTSC mode, it cannot properly process the RGB video signal from the endoscope. Consequently whenever the physician wishes to switch from the endoscope view to the fluoroscope view for archiving an image on magnetic disk, the physician must instruct the photo archiving computer to change its video mode of operation from RGB to NTSC, and when he wishes to switch back to the endoscope video signal he must instruct the photo archiving computer to change its video mode of operation from NTSC back to RGB. This selection of the video mode in which the photo archiving computer is to operate is conventionally accomplished by entering a predefined keyboard sequence. For example, in the aforementioned Olympus Image Manager, which is presently in widespread use, the physician toggles back and forth between RGB and NTSC video modes by entering a [control]-V-keystroke sequence on the photo archiving computer's keyboard. Thus whenever the physician wishes to switch from the endoscope view to the fluoroscope view for archiving an image on magnetic disk, the physician must enter a keystroke sequence to instruct the (photo archiving computer to select the appropriate video mode for operation while either he or an assistant activates the fluoroscope X-ray generator, captures the desired image(s), then deactivates the X-ray generator.

Thus there is a need for a video component for storing and archiving video images on magnetic disk which will select the appropriate video mode for operation without intervention by the physician.

There is a further need for a video component for storing and archiving video images on magnetic disk which will select the appropriate video mode for operation without intervention by the physician while minimizing exposure of the patient and attending medical personnel to X-rays from the fluoroscope.

SUMMARY OF THE INVENTION

Stated generally, the present invention comprises an apparatus for use with a video component for storing and archiving video images on magnetic disk which selects the appropriate video mode for operation without intervention by the physician or his assistant. The invention relates to a video component having a video input capable of operating in either of two video modes. The video component has a data input device operatively associated with it and is responsive to a predetermined signal from the data input device for selecting from between the first video mode and the second video mode for operation. However, to eliminate the requirement that the physician or an assistant manually generate the predetermined signal from the data input device, the present invention includes a means associated with the video component and with a footswitch and responsive upon actuation of the footswitch for sending the predetermined signal to the video component to select from between the first video mode and the second video mode for operation.

In a preferred embodiment the present invention relates to a photo archiving computer for archiving and storing still video images on a suitable storage medium, for example, the Olympus Image Manager. The Olympus Image Manager is capable of operating in either the RGB or the NTSC video mode. The RGB video signal from an endoscope and the NTSC video signal from a fluoroscope are input into the photo archiving computer. The photo archiving computer has a keyboard associated with it and is responsive to a predetermined keyboard sequence for selecting from between the RGB and NTSC video modes for operation. However, to eliminate the requirement that the physician or his assistant press keys on a keyboard, the present invention includes a means associated with the video component and with the footswitch which actuates the X-ray generator of the fluoroscope which sends a signal to the photo archiving computer corresponding to the predetermined keyboard sequence when the fluoroscope footswitch is actuated to select the NTSC video mode for operation. When the fluoroscope footswitch is released, the means sends a second signal to the photo archiving computer corresponding to the predetermined keyboard sequence to reselect the RGB video mode for operation.

Thus it is an object of the present invention to provide an improved apparatus for controlling the video mode in which a video component operates.

It is another object of the present invention to provide an apparatus for controlling a video component whose video mode of operation is normally controlled by a data input device, wherein the apparatus does not require manual operation of the data input device.

It is a further object of the present invention to provide an improved apparatus for storing and archiving video images on a storage medium wherein the apparatus can operate in either of two incompatible video modes.

Still another object of the present invention is to provide an apparatus for use in surgical procedures involving endoscopy and fluoroscopy wherein the endoscope video signal is in a first video format, the fluoroscope video signal is in a second format, and both video signals are input into a component for archiving and storing still video images, wherein the component is automatically switched between the two video modes of operation upon actuation of the footswitch which controls the fluoroscope X-ray generator.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
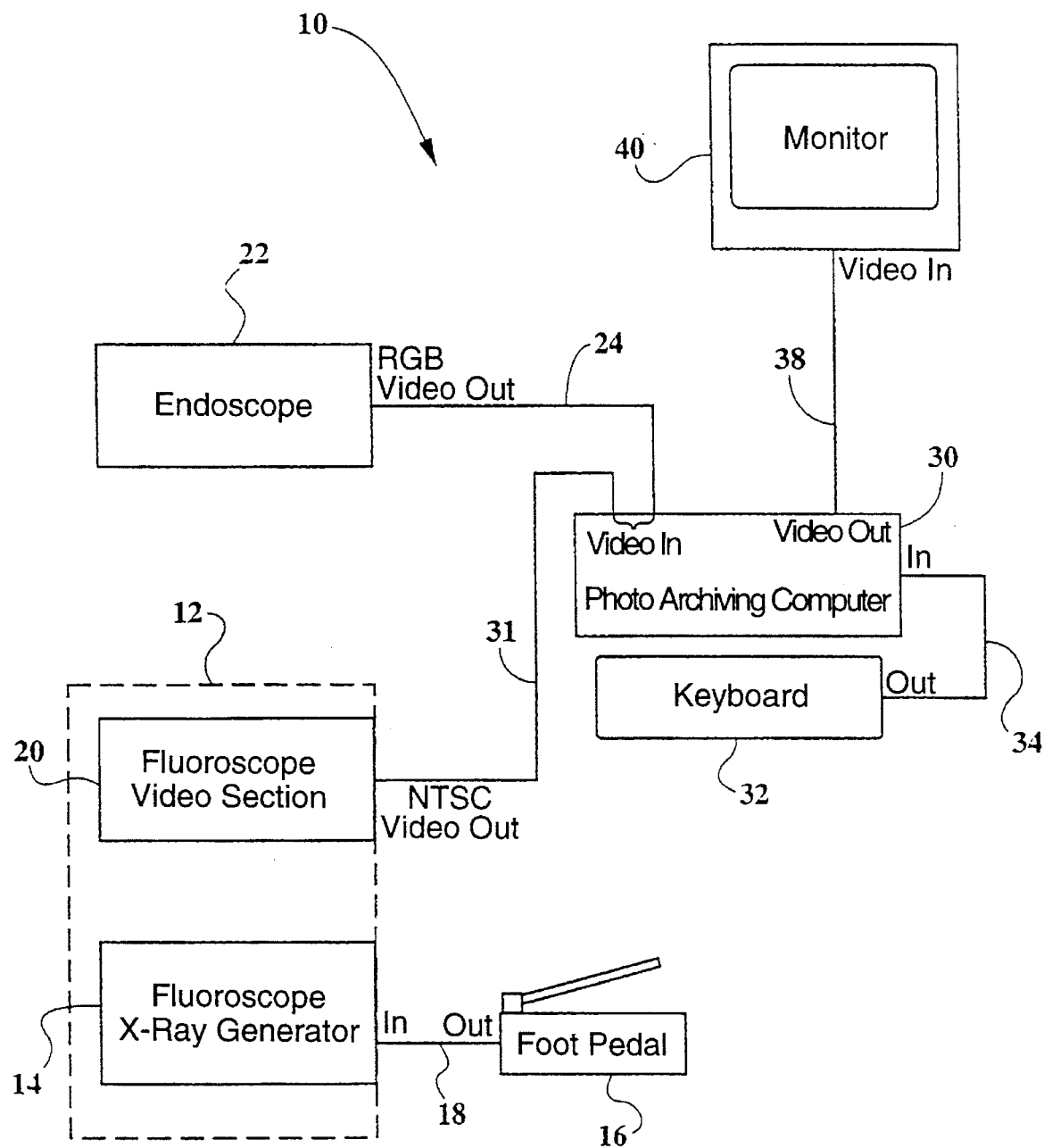
FIG. 1 is a schematic diagram of a PRIOR ART apparatus for use with endoscopy and video fluoroscopy.

Referring now to the drawings, in which like numerals indicate like elements throughout the several views, FIG. 1 is a schematic diagram of an illustrative prior art apparatus 10 for use with endoscopy and video fluoroscopy. A fluoroscope 12 of conventional design includes a fluoroscope X-ray generator 14 actuated by a foot pedal 16 connected to the X-ray generator via a signal path 18. The fluoroscope 12 is designed such that the X-ray generator 14 emits X-rays only while the foot pedal 16 is depressed, and when the physician releases foot pressure the switch 16 will automatically open. In this manner it is difficult for the X-ray generator 14 to be accidentally left actuated, and exposure of the patient and attendant medical personnel to large doses of radiation is thereby minimized.

The fluoroscope 12 further includes a fluoroscope video section 20 comprising a camera and attendant video processing circuitry. As has already been indicated, X-rays are projected through a patient onto a fluorescent screen which, when subjected to X-radiation, produces a direct image of the object under investigation. Because the image on the fluorescent screen is usually so faint that it is difficult to visualize with the unaided eye, the screen image is photographed with a sensitive video camera. The video signal is then processed to increase the brightness of the image and is output in NTSC video format to a fluoroscope video monitor. (not shown). All of the foregoing aspects of the fluoroscope 12 are well known, as will readily be appreciated by those skilled in the art.

The prior art apparatus 10 further comprises a video endoscope 22 of conventional design. The video endoscope of the disclosed embodiment is the Olympus CV-100, though it will be understood that any suitable video endoscope may be employed. The video endoscope 22 is capable of generating an output signal in either NTSC or RGB mode, though higher resolution is attained in RGB mode and is thus preferred over NTSC mode.

The video output from the video endoscope 22 in RGB mode is directed along a signal path 24 to a photo archiving computer 30, such as the Olympus Image Manager. Similarly, a video output from the video section 20 of the fluoroscope is output in NTSC format along a signal path 31 to the photo archiving computer 30. The photo archiving computer 30 is essentially a computer which archives and stores still video images on a suitable storage medium, such as magnetic disk. The photo archiving computer 30 has a keyboard 32 connected thereto by a signal path 34. The keyboard 32 is conventionally used to enter data associated with the stored image, such as the patient's name, the date of the procedure, and so forth. The photo archiving computer 30 associates the entered data with the video image, both as the image is archived and as the image is displayed on a video monitor.

The video signal from the photo archiving computer 30 is output in RGB format via a signal path 38 to a monitor 40, for real-time viewing of the procedure by the physician. Optionally, a still-photograph unit (not shown), such as the Sony Mavigraph, can be placed along the signal path 38 to make hard copy photographs of the procedure at any particular moment. Also, a video cassette recorder (not shown) can optionally be placed along the signal path 38 to make a recording of the video images seen by the physician.

While the still-photograph unit and the VCR will be found in many applications, it will be understood that these components are not necessary to the function of the present invention.

Still referring to the prior art arrangement of FIG. 1, as has been previously suggested the preferred video mode for the video signal output by the video endoscope 22 is RGB mode, because of its increased resolution. On the other hand, the video signal output from the fluoroscope 12 is in NTSC video format, which is incompatible with the photo archiving computer 30 when operating in RGB mode. Accordingly, for the photo archiving computer 30 to capture and to archive images from both the video endoscope 22 and the fluoroscope 12, it is necessary to instruct the photo archiving computer 30 in which video format it is to operate. This instruction is typically made by entering a predefined keystroke sequence onto the keyboard 32 of the the photo archiving computer 30. In the case of the Olympus Image Manager, the keystroke sequence [control]-V toggles the photo archiving computer 30 back and forth between RGB and NTSC modes. Consequently, when the physician has the photo archiving computer 30 set in RGB mode to accept the video signal for video endoscope 22 and wishes to archive a video image from the fluoroscope 12, the predefined keystroke sequence must be input into the photo archiving computer 30 to toggle the video mode from RGB to NTSC. Concurrently with toggling the video mode of the photo archiving computer 30, the physician must step on the foot pedal 16 to actuate the X-ray generator 14 of the fluoroscope 12. Further, when the video fluoroscope view is deselected, the keystroke sequence must again be input into the photo archiving computer 30 to toggle the video mode back to RGB. Concurrently the physician must release the foot pedal 16 to deactivate the fluoroscope X-ray generator 14 to prevent overexposure of the patient and attending medical personel to radiation.

In the prior art arrangement of FIG. 1, it will be appreciated that the video input which is being accepted by the photo archiving computer 30 at any given moment is the video signal which is being output to the monitor 40. Accordingly, toggling the photo archiving computer 30 between RGB and NTSC video modes has the incidental effect of toggling between the endoscope and fluoroscope views on the video monitor 40.

Figure 2:
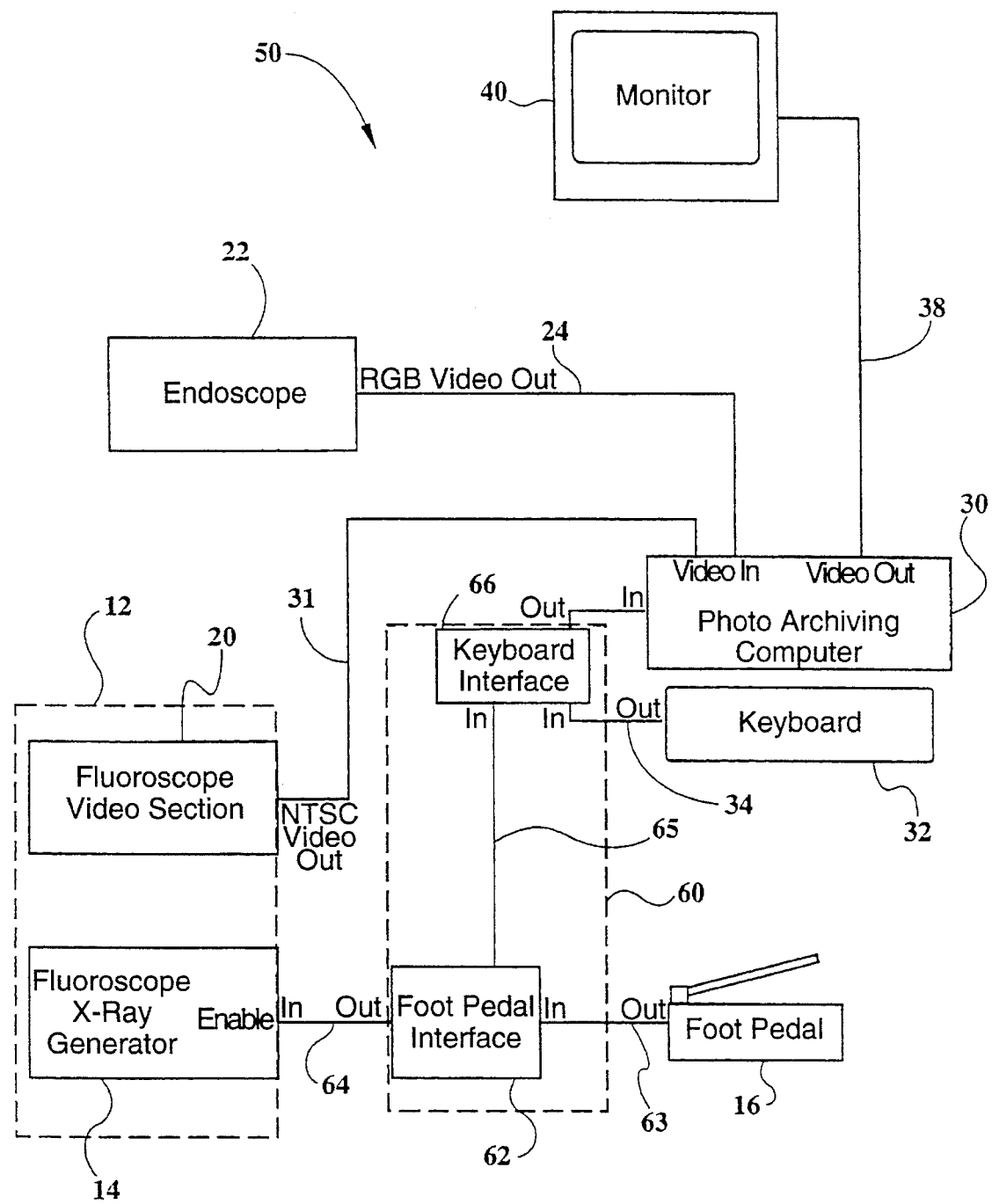
FIG. 2 is a schematic diagram of a first embodiment of an apparatus for use with endoscopy and video fluoroscopy, according to the present invention.

FIG. 2 illustrates a first embodiment of an apparatus 50 according to the present invention, for use in surgical modalities involving video endoscopy and video fluoroscopy. The apparatus 50 includes an automatic switching apparatus 60 for automatic switching between video modes as the fluoroscope 12 is enabled. The automatic switching apparatus 60 includes a foot pedal interface 62 connected to the foot pedal 16 by a signal path 63. The signal transmitted along signal path 63 is passed through the foot pedal interface 62 and sent to the X-ray generator 14 of the fluoroscope 12 by a signal path 64. The foot pedal interface 62 detects the presence of an actuating current between the foot pedal 16 and the X-ray generator 14. In response to a detected "foot pedal down" state, the foot pedal interface 62 sends a first signal via a signal path 65 to a keyboard interface 66, which is interposed along the signal path 34 between the keyboard 32 and the photo archiving computer 30. In response to this first signal, the keyboard interface 66 disables the keyboard 32 and sends a signal to the photo archiving computer 30 corresponding to the predefined keystroke sequence for enabling NTSC video mode. In the case of the Olympus Image Manager, the keyboard interface 66 is programmed to send a signal corresponding to the [control]-V keystroke sequence. When the foot pedal is released, the foot pedal interface 62 will detect the change in the actuating current between the foot pedal 16 to the X-ray generator 14. In response to a detected "foot pedal up" state, the foot pedal interface 62 sends a second signal via the signal path 65 to the keyboard interface 66. In response to this second signal, the keyboard interface 66 sends a signal to the photo archiving computer 30 corresponding to the predefined keystroke sequence for enabling RGB video mode. In the case of the Olympus Image Manager, the [control]-V keystroke sequence toggles the video mode back to RGB mode.

Figure 3:
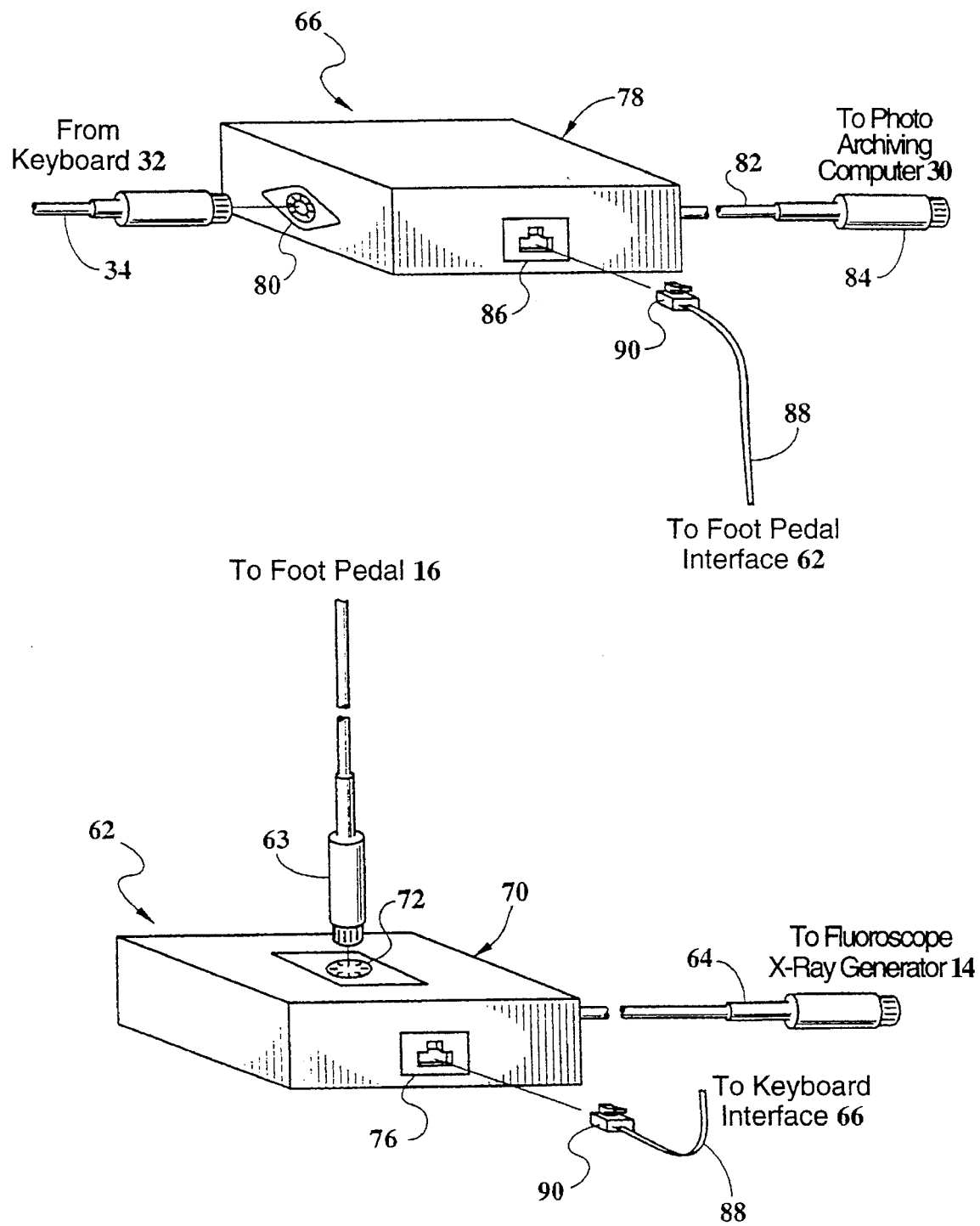
FIG. 3 is a perspective view of a foot pedal interface and a keyboard interface of the apparatus of FIG. 2.

FIG. 3 shows the foot pedal interface 62 and keyboard interface 66 of the automatic switching apparatus 60. The foot pedal interface 62 comprises a box 70 having a female Switchcraft flush mount connector 72 mounted on its upper surface. The cable comprising the signal path (18 in FIG. 1) from the foot pedal 16 is disconnected from the X-ray generator 14 of the fluoroscope 12 and is plugged into the connector 72 to comprise the signal path 63. A cable comprising the signal path 64 runs from the box 70 and plugs into the X-ray generator 14 of the fluoroscope 12. A female RJ 11 phone jack 76 is mounted on one side of the box 70.

The keyboard interface 66 comprises a box 78 having a female keyboard jack 80 mounted on one end. The cable comprising the signal path 34 between the keyboard 32 and the photo archiving computer 30 is disconnected from the photo archiving computer and plugged into the female keyboard jack 80 of the keyboard interface 66. A cable 82 running out of the box 78 has a keyboard male plug 84 at its end which is plugged into a corresponding female jack in the photo archiving computer 30. A female RJ 11 phone jack 86 is mounted on one side of the box 78. A length of telephone cable 88 having male RJ 11 connectors 90 at both ends interconnects the foot pedal interface 62 and keyboard interface 66 by plugging the male connectors 90 into the corresponding female jacks 76, 86.

Figure 4:
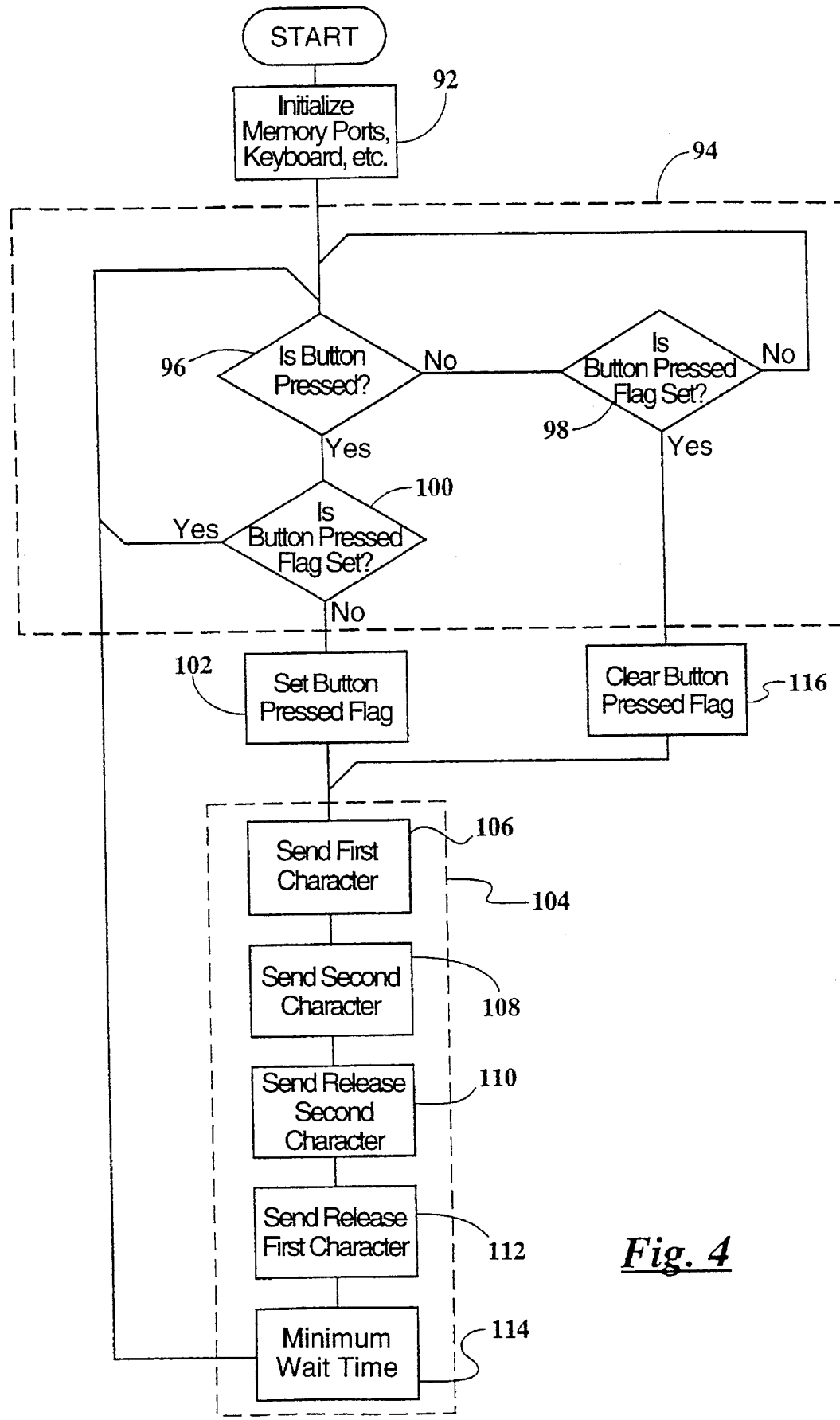
FIG. 4 is a flow chart illustrating the operation of a device for automatic switching between video modes, which device is a component of the apparatus of FIG. 2.

FIG. 4 is a flow chart illustrating the operation of the automatic switching apparatus 60 for automatic switching between video modes. When the automatic switching apparatus 60 is first powered up, it initializes the memory ports, the keyboard, flags, and so forth, as shown at 92. The switching apparatus 60 then goes into a detection loop 94, in which it detects whether the foot pedal 16 is depressed, as shown at 96. If not, the switching apparatus 60 detects whether a "button pressed" flag is set, as indicated at 98. If not, then the switching apparatus 60 stays in the detection loop 94 and takes no action. If the switching apparatus 60 detects that the foot pedal 16 is depressed, it then checks at 100 whether a "button pressed" flag is set, i.e. whether the foot pedal 16 was already depressed in the previous loop. If so, then the switching apparatus 60 remains in the detection loop 94 and takes no action.

However, if the switching apparatus 60 detects at 96 that the foot pedal 16 has been depressed and detects at 100 that the "button pressed" flag was not previously set (i.e. that the pedal has just been depressed), then the switching apparatus sets the "button pressed" flag at 102 and then goes into a "send character" sequence 104. Similarly, if the switching apparatus 60 detects at 96 that the foot pedal 16 is not depressed and detects at 98 that the "button pressed" flag was previously set (i.e. that the pedal has just been released), then the switching apparatus goes into the "send character" sequence 104.

When the detection loop 94 has detected either that the foot pedal 16 has been depressed or that foot pedal has been released, the "send character" sequence 104 is invoked. A signal corresponding to the first character, the [control] character, is sent to the photo archiving computer 30, as shown at 106. A signal corresponding to the second character, the "V" character, is then sent to the image manger 30, as shown at 108. A signal corresponding to the release of the second character is then sent to the photo archiving computer 30, as shown at 110. A signal corresponding to the release of the first character is then sent to the photo archiving computer, as shown at 112. The procedure then pauses at 114 for a minimum wait time to prevent switch contact "bounce" from causing the keyboard interface 66 to send multiple sets of commands in short successsion. After the minimum wait time control is passed from the "send character" sequence 104 back to the detection loop 94, whereupon the switching apparatus 60 awaits the next action of the foot pedal 16.

Still referring to FIG. 4, a similar sequence occurs when a depressed foot pedal 16 is released. So long as the foot pedal 16 is depressed, the "button pressed" decision at 96 will result in a "yes" answer, and the "button pressed flag set" decision at 100 will also yield a "yes" answer. The switching apparatus 60 thus remains in the detection loop 94 and takes no action. But when the foot pedal 16 is released, the "button pressed" decision at 96 becomes "no," the "button pressed'flag set" decision at 98 is no, and control passes out of the detection loop 94. The button press flag is cleared at 116, and control is passed to the "send character" sequence 104. Thus releasing the foot pedal 16 causes a second [control]-V signal to be sent to the photo archiving computer 30, toggling the video mode from NTSC back to RGB.

Figure 5:
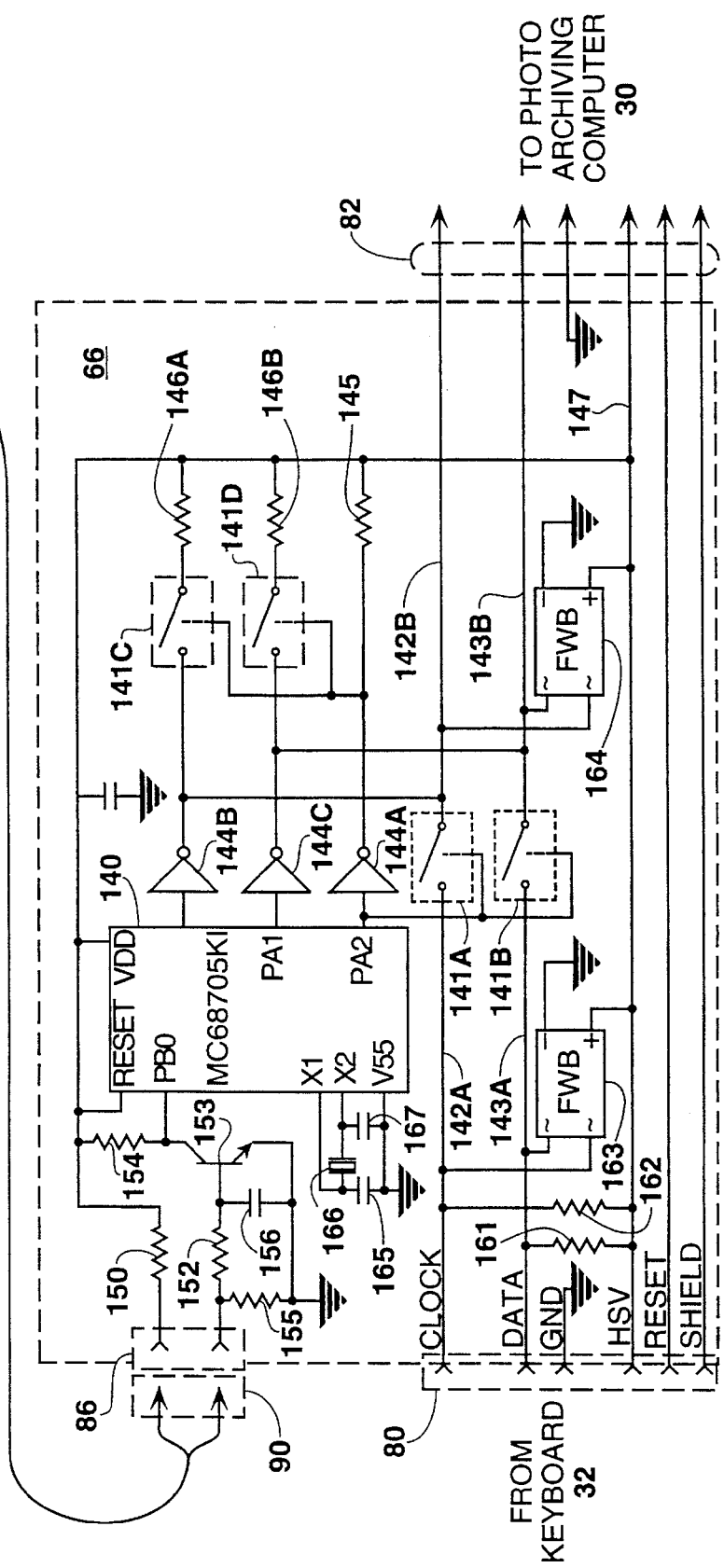
FIG. 5 is an electrical schematic diagram of the device for automatic switching between video modes which is the subject of the flow chart of FIG. 4.

FIG. 5 is an electric schematic diagram of the foot pedal interface 62 and the keyboard interface 66 used to accomplish automatic switching between video modes. Two of the lines from foot pedal 16 are passed via connector 72 and cable 74 to fluoroscope without alteration. A third conductor is routed from connector 72 through resistor 130 and then to cable 74. When foot pedal 16 is closed a current will flow through resistor 130, thereby developing a voltage across resistor 130. Resistor 130 is connected in parallel with the input diode 131A of an optoisolator 131. In the preferred embodiment optoisolator 131 is a Darlington output optoisolator such as the 4N33. The outputs of optoisolator 131 are connected through a full wave bridge (FWB) 132 to connector 76. Bridge 132 prevents damage to optoisolator 131 in the event of a reverse polarity connection. The base of transistor 131B of optoisolator 131 is connected to the emitter by the parallel combination of resistor 133 and capacitor 134. Resistor 133 is a pull-down resistor to assure that leakage current does not bias transistor 131B into the on state. Capacitor 134 is a noise filtering capacitor. In the preferred embodiment, resistor 130 is formed of two resistors, one being 27 ohms and ½ watt, and the other being 75 ohm ½ watt. Resistor 133 is 1 Megohm, and capacitor 134 is 0.01 microfarads. Full wave bridge 132 is conveniently constructed of four 1N4148 diodes. When foot pedal 16 is closed and a current flows through the resistor 130, the LED 131A will be turned on, thereby turning on transistor 131B, thereby allowing current to flow between the conductors of connector 76. When foot pedal 16 is not depressed then there will be no current flowing through resistor 130, LED 131A and transistor 131B will be turned off, and an open circuit will be present between the two conductors of connector 76. Keyboard interface 66 passes the ground, +5 volt, reset and shield lines from keyboard 32 to photo archiving computer 30 without alteration via connector 80 and cable 82. However, signals on the clock and data lines from keyboard 32 may be altered by keyboard interface 66 before being passed to photo archiving computer 30. More particularly, an analog switch 141A is used to break the clock line 142 into parts 142A and 142B and another analog switch 141B is used to break the data line 143 into parts 143A and 143B. In the preferred embodiment, switches 141A and 141B are two of the four analog switches in a type CMOS 4066 quad analog switch device. Switches 141A and 141B are controlled by the PA2 (Port A, bit 2) output of microprocessor 140. When the PA2 output is a logic zero then switches 141A and 141B present an open circuit, thereby disconnecting the clock and data output of keyboard 32 from the clock and data inputs of photo archiving computer 30. However, if the PA2 output is a logic one then switches 141A and 141B are closed so the clock signals and data signals from keyboard 32 are presented to photo archiving computer 30. Normally, the PA2 output of microprocessor 140 is a logic one so that switches 141A and 141B are normally closed. The PA2 output of microprocessor 140 is also connected to the input of an open collector inverter 144A, which is conveniently implemented as one of a set of three-input NAND gates with open collector outputs, such as a 74LS12 device. The output of gate 144A is connected to a pull-up resistor 145 and also to the control inputs of two analog switches 141C and 141D. The PA0 and PA1 outputs of microprocessor 140 are connected to the inputs of inverters 144B and 144C, respectively. The output of inverter 144B is connected to one end of switch 141C and also to clock signal line 142B. The other end of switch 141C is connected to pull-up resistor 146A. Similarly, the output of inverter 144C is connected to one end of switch 146B and to data signal line 143B. The other end of switch 141D is connected to pull-up resistor 146B. Pull-up resistors 145, 146A and 146B are connected the +5 volt supply line 147.

When the PA2 output of microprocessor 140 is a logic zero then switches 141A and 141B will be opened and switches 141C and 141D will be closed. This places a logic one onto lines 142B and 143B, subject to being pulled down to a logic zero by inverters 144B and 144C. Thus, microprocessor 140 can send clock and data signals over lines 142B and 143B by pulsing its PA0 and PA1 outputs so as to cause inverters 144B and 144C to pull down and release lines 142B and 143B, respectively. This allows microprocessor 140 to send signals, such as [control]-V, to the photo archiving computer 30. When microprocessor 140 is not sending signals to photo archiving computer 30 then the PA0 and PA1 outputs are set to a logic zero so that the outputs of inverters 144B and 144C are open circuits and do not affect the clock and data lines 142 and 143.

Microprocessor 140 sends signals to photo archiving computer 30 in response to depressions of foot pedal 16. Microprocessor 140 detects depressions of foot pedal 16 as follows. The +5 volt supply line 147 is connected through a current limiting resistor 150 to one of the conductors of connector 86. The other conductor of 86 is connected through resistor 152 to the base of transistor 153. The collector of transistor 153 is connected to the PB0 (Port B, bit 0) input of microprocessor 140 and also to one end of a pull-up resistor 154. The other end of pull-up resistor 154 is connected to 5 volt line 147. As previously explained, foot pedal interface 62 is connected to keyboard interface 66 via cable 88 which has connectors 90 on both ends. A connector 90 on one end of cable 88 plugs into connector 86 of keyboard interface 66. Therefore, when foot pedal 16 is closed foot pedal interface 62 will place a short between the conductors of cable 88. This causes transistor 153 to be turned on and to place a logic zero at the PB0 input of microprocessor 140. When foot pedal 16 is released the conductors of cable 88 will no longer be shorted together by optoisolator 131, transistor 153 will be turned off, and resistor 154 will place a logic one at the PB0 input of microprocessor 140. The emitter of transistor 153 is connected to circuit-ground. In addition, a capacitor 156 is connected between the base and emitter of transistor 153 so as, in conjunction with resistor 152, to form a lowpass filter and provide noise immunity. A resistor 155 is connected between circuit ground and the end of resistor 152 connected to connector 86. Resistor 155 is a pull-down resistor to prevent leakage current of transistor 153 from turning transistor 153 on.

Keyboard interface 66 draws operating power from photo archiving computer 30 via circuit ground and via the +5 volt supply line 147. Capacitor 160, connected between circuit ground and supply line 147, provides for noise filtering of the supply line. Two resistors, 161 and 162, are connected to clock and data lines 142A and 143A, respectively, so as to pull these lines up to a logic one when switches 141A and 141B are open. Full wave bridge rectifiers 163 and 164, conveniently constructed of four 1N4148 diodes, are connected between +5 volt supply line 147, the circuit ground, clock lines 142A and 142B and data lines 143A and 143B. Bridges 163 and 164 act as surge suppressers to limit the magnitude of voltage spikes which may appear on clock and data lines 142 and 143 by shunting positive spikes to the +5 volt supply line 147 and shunting negative spikes to circuit ground.

Capacitors 165 and 167 and crystal 166 are connected to the X1 and X2 crystal oscillator inputs of microprocessor 140. In the preferred embodiment, resistors 150, 152, 161 and 162 each have a value of 10 kohms. Resistor 145 has a value of 4.7 kohms. Resistor 155 has a value of 51 kohms. Resistors 146A and 146B each have a value of 3 kohms. Capacitor 156 has a value of 0.1 microfarad, capacitor 160 has a value of 5 microfarads, and capacitors 165 and 167 each have a value of 27 picofarads. Crystal X1 is preferably a 3.58 MHz (approximately) color TV subcarrier crystal.

Figure 6A:
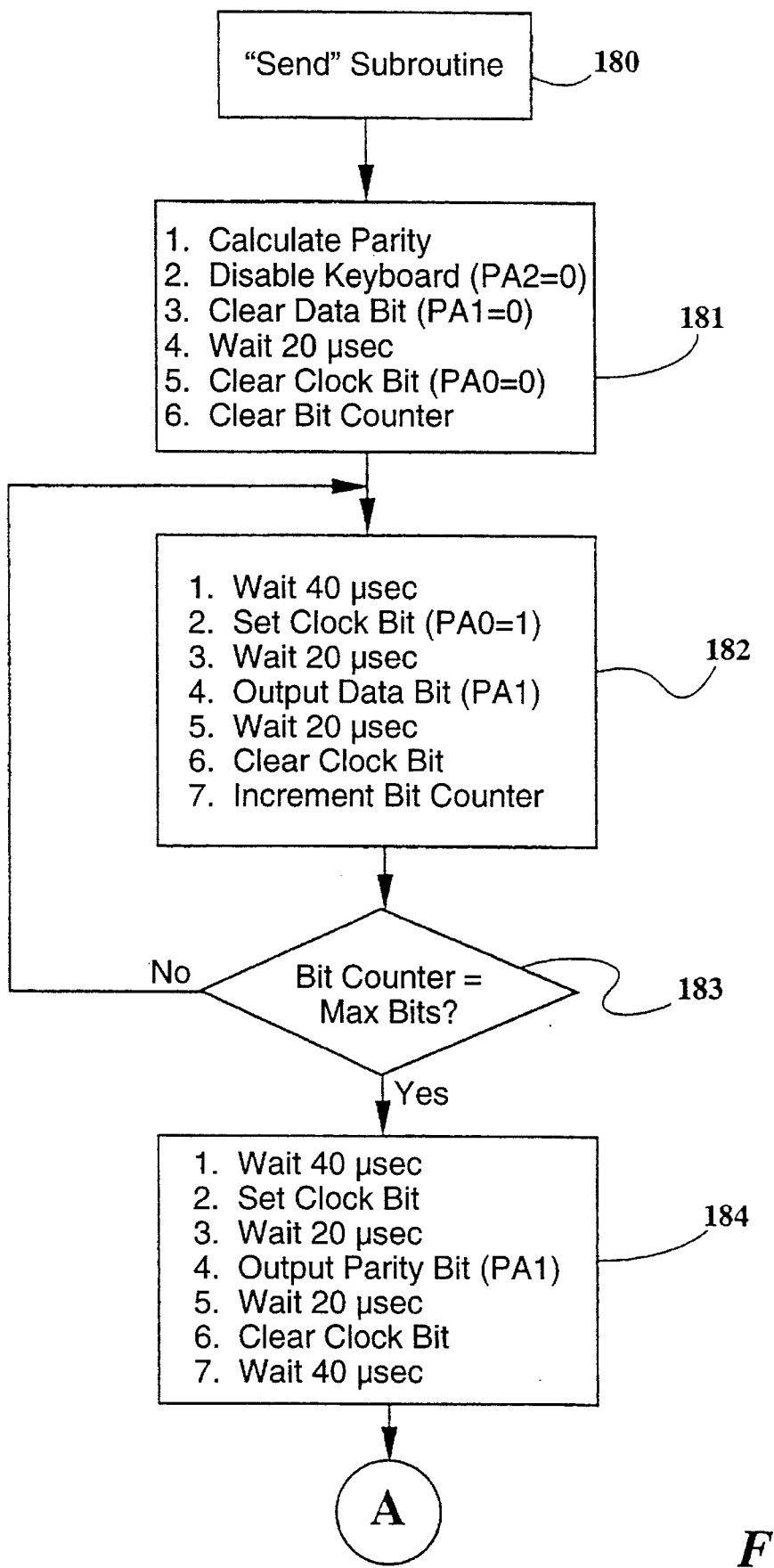
FIGS. 6A and 6B are a flow chart illustrating the operation of the send sequence employed by the automatic switching device of FIG. 5.
Figure 6B:
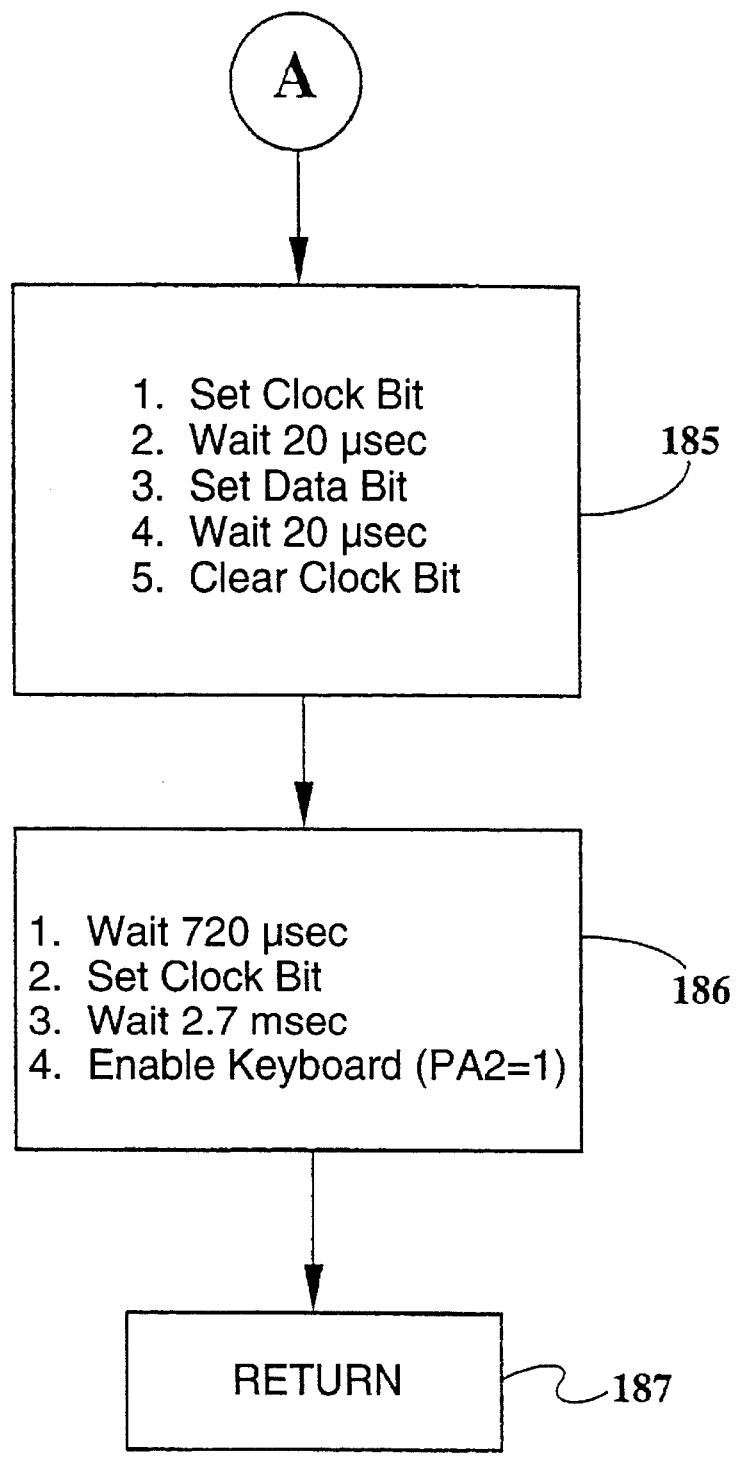

FIG. 6 is a flowchart illustrating the operation whereby the microprocessor 140 sends a sequence to the photo archiving computer 30, such as the send sequence referred to in steps 104, 108, 110, and 112 of FIG. 4 and, more particularly, the [control]-V sequence.

The send sequence is preferably implemented as a subroutine 180 which is executed by microprocessor 140. In step 181 microprocessor 140 calculates the parity of the word to be sent, disables the keyboard by setting output PA2 to a logic zero, clears the data bit by setting output PA1 to a logic zero, waits 20 microseconds, clears the clock bit by setting output PA0 to a logic zero, and clears a bit counter. It will be appreciated that it is not necessary to actually calculate the parity but, if preferred, all of the bits of the word to be sent, including the parity bit, can be stored in memory, such as read only memory or random access memory, in microprocessor 140. Also, the bit counter is a register in microprocessor 140 which is used by microprocessor 140 to determine if all the data bits for a particular word have been sent. Lastly, it will be noted that the processed described herein employs several "wait" steps. These wait steps are implemented by dummy operations which waste clock cycles, and are used so that microprocessor 140 simulates the clock and data rate of AT-style keyboard 32. Once the initialization procedures in step 181 have been completed microprocessor 140 proceeds to 182.

In step 182 microprocessor 140 waits for 40 microseconds, then sets the clock bit by setting its PA0 output to a logic one, waits 20 microseconds, outputs a data bit for the word to be sent by setting its PA1 output to a logic zero or a logic one, as appropriate for the particular data bit of the particular word being sent, waits 20 microseconds, clears the clock bit, and then increments the bit counter.

At decision 183 microprocessor 140 tests the bit counter to determine if all of the bits (max bits) have been sent for the desired word. If all of the bits for a desired word have not been sent then microprocessor 140 returns to step 182. On the first pass through step 182 after entering subroutine 180 microprocessor 140 will send the first bit of the desired word. On each subsequent pass through step 182 microprocessor 140 will send the next bit in the desired word. If the word being sent has a format of seven data bits, a parity bit and a stop bit, then after seven passes through step 182 microprocessor 140 will have sent all of the data bits for the desired word. Microprocessor 140 will then exit from decision 183 to begin step 184.

In step 184 microprocessor 140 sends the parity bit for the word which has just been sent. This is done by waiting 40 microseconds, setting the clock bit, waiting 20microseconds, outputting the parity bit via PA1, waiting 20 microseconds, clearing the clock bit, and then waiting 40 microseconds.

Microprocessor 140 then proceeds to step 185 wherein it sends the stop bit for the word which has just been sent. This is done by setting the clock bit, waiting 20 microseconds, sending the stop bit via PA1, waiting 20 microseconds, and then clearing the clock bit.

Finally, in step 186 microprocessor 140 returns control of the clock and data lines to keyboard 32. This is done by waiting 720 microseconds, setting the clock bit, waiting an additional 2.7 milliseconds, and then enabling the keyboard 32 by setting output PA2 to be a logic one. Then, in step 187 microprocessor 140 returns to the main process.

From the above, it will be seen that the present invention sends a [control]-V sequence to photo archiving computer 30 each time foot pedal 16 is depressed or released. Therefore, photo archiving computer 30 receives a signal to switch between RGB and NTSC modes as if the user had entered a [control]-V command directly from keyboard 32. In the preferred embodiment only the clock and data lines from keyboard 32 are interrupted by keyboard interface 66. Operating power to keyboard 32 is not interrupted so keyboard 32 is not adversely affected by keyboard interface 66.

In operation, the apparatus 10 functions as follows. In its normal state the photo archiving computer 30 operates in RGB mode and routes the video signal from the endoscope 22 to the monitor 40. When the foot pedal interface 62 detects the "foot pedal down" state, a signal is sent along signal path 65 to the keyboard interface 66. In response to this signal, the keyboard interface 66 transmits a signal corresponding to the [control]-V keystroke sequence to the photo archiving computer 30, toggling the photo archiving computer from RGB mode to NTSC mode. This action selects the video signal from the fluoroscope 12 for storing and archiving and outputs the fluoroscope signal to the video monitor 40.

When the foot pedal 16 is released, the foot pedal interface 62 detects the "foot pedal up" state and transmits another signal along signal path 65 to the keyboard interface 66. In response to this signal, the keyboard interface 66 transmits a second signal corresponding to the [control]-V keystroke sequence to the photo archiving computer 30, toggling the photo archiving computer from NTSC mode back to RGB mode. This action causes the photo archiving computer 30 to reselect the video signal from the endoscope 22 for archiving and storage and for output to the video monitor 40. Thus actuation of the foot pedal 16 not only actuates the X-ray generator 14 but also automatically selects the proper video format for the photo archiving computer 30 and automatically selects the proper video signal for display on the monitor 40, all without intervention by the physician or other operating room personnel.

While the first embodiment 50 has been disclosed with respect to an arrangement comprising an in-line foot pedal interface 62 for detecting a "pedal down" state and sending a signal to the keyboard interface 66, it will be appreciated that similar results could be obtained by eliminating the in-line foot pedal interface 62 in favor of a foot pedal having a second switch associated therewith.

Figure 7:
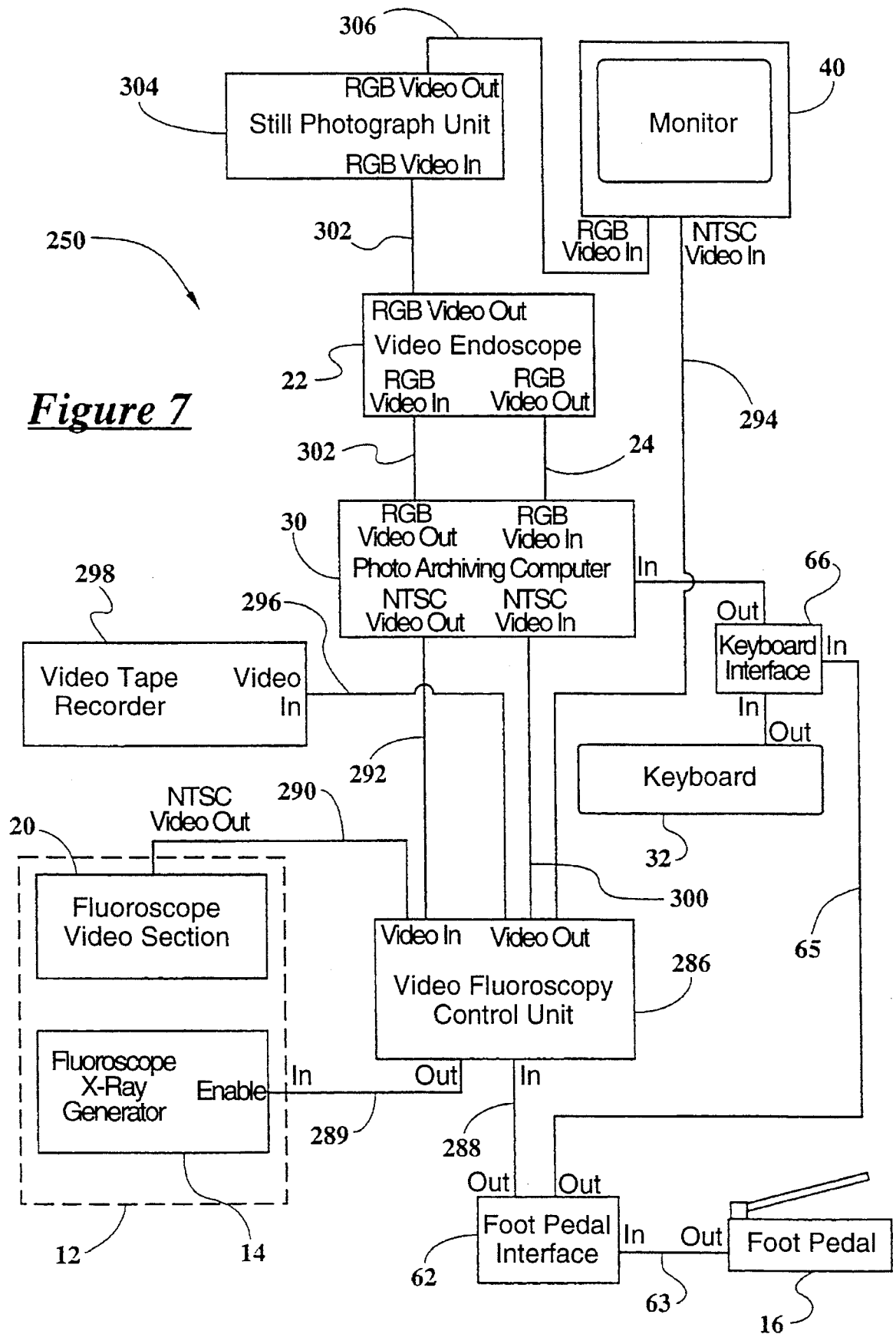
FIG. 7 is a schematic diagram of a second embodiment of an apparatus for use with endoscopy and video fluoroscopy, according to the present invention.

FIG. 7 shows an alternate embodiment of an apparatus 250 for use in surgical modalities involving video endoscopy and video fluoroscopy, according to the present invention. The apparatus 250 employs a video fluoroscopy control unit 286 of the type disclosed in U.S. Pat. Nos. 4,993,404 and 5,127,394, which patents are incorporated herein by reference. The foot pedal 16 is connected to the foot pedal interface 62 by means of the signal path 63. In turn, the foot pedal interface 62 is connected to the video fluoroscopy control unit 286 by means of a signal path 288. A signal entering the video fluoroscopy control unit 286 by means of the signal path 288 is passed through the video fluoroscopy control unit 286 and transmitted to the fluoroscope X-ray generator 14 by means of a signal path 289. The foot pedal interface 62 also communicates via signal path 65 with the keyboard interface 66 in the same manner described above with respect to the first embodiment 10.

The fluoroscope 12 outputs a video signal in NTSC format along a signal path 290 to the video fluoroscopy control unit 286. A video signal from the video endoscope 22 in RGB format is transmitted along the signal path 24 to the photo archiving computer 30. The video output from the photo archiving computer 30 in NTSC format is sent via signal path 292 to the video fluoroscopy control unit 286. A first video output from the video fluoroscopy control unit 286 is sent in NTSC format via a signal path 294 to the monitor 40. A second video output from the video fluoroscopy control unit 286 is transmitted along a signal path 296 to a video cassette recorder 298. A third video output from the control unit 286 is transmitted along a signal path 300 to the photo archiving computer 30. As disclosed in the aforementioned U.S. Pat. Nos. 4,993,404 and 5,127,394, the video fluoroscopy control unit 286 normally outputs the video signal of the video endoscope 22 in NTSC format via signal path 294 to the monitor 40. In addition, the video fluoroscopy control unit 286 normally outputs the video signal of the video endoscope 22 to the photo archiving computer 30 via the signal path 300. However, when the foot pedal 16 is depressed, the video fluoroscopy control unit 286 detects the "foot pedal down" state and selects the video signal from the fluoroscope 12 for output to the video monitor 40 and the photo archiving computer 30. When the foot pedal 16 is released, the video fluoroscopy control unit 286 detects the "foot pedal up" state and reselects the video signal from the video endoscope 22 for output to the video monitor 40.

A second video output, this one in RGB format, is transmitted from the photo archiving computer 30 along a signal path 302 to a still photograph unit 304, such as the Sony Mavigraph. In the disclosed embodiment, the signal path 302 passes back through the video endoscope 22 for convenience of connection, but it will be appreciated that a direct connection between the photo archiving computer 30 and the still photograph unit 304 is also possible. The RGB signal is then transmitted from the still photograph unit 304 via signal path 306 to the monitor 40.

In operation, the photo archiving computer 30 normally operates in RGB mode and selects the RGB signal arriving along signal path 24 from the video endoscope 22. Also, the video fluoroscopy control unit 286 normally selects the NTSC signal from the video endoscope 22 arriving along signal path 292 for output to the monitor 40 via signal path 294. When the foot pedal 16 is depressed, the foot pedal interface 62 detects the "foot pedal down" state and transmits a signal along signal path 65 to the keyboard interface 66. In response to this signal, the keyboard interface 66 transmits a signal corresponding to the [control]-V keystroke sequence to the photo archiving computer 30, toggling the photo archiving computer from RGB mode to NTSC mode. The photo archiving computer 30 now selects the NTSC signal from the video fluoroscope 12 arriving via the video fluoroscopy control unit 286 along signal path 300. Simultaneously the video fluoroscopy control unit 286 detects the "pedal down" state and switches to the video signal from the fluoroscope 12 for output to the video monitor 40. Thus actuation of the foot pedal 16 serves to toggle the video mode of the photo archiving computer 30 to select the NTSC video signal from the fluoroscope and also to select the video signal from the fluoroscope 12 for display on the video monitor 40.

When the foot pedal 16 is released, the foot pedal interface 62 detects the "foot pedal up" state and transmits a signal along signal path 65 to the keyboard interface 66. In response to this signal, the keyboard interface 66 transmits a second signal corresponding to the [control]-V keystroke sequence to the photo archiving computer 30, toggling the photo archiving computer from NTSC mode back to RGB mode. Simultaneously the video fluoroscopy control unit 286 detects the "foot pedal up" state and reselects the video signal from the endoscope 22 for output to the video monitor 40. Thus releasing the foot pedal serves to toggle the video mode of the photo archiving computer 30 to select the RGB signal from the endoscope 22 and also to select the NTSC video signal from the endoscope 22 for display on the video monitor 40.

As will be appreciated, in each of the foregoing embodiments the physician is relieved of the responsibility for entering a keyboard command to put the photo archiving computer 30 into the proper video mode. In addition, the proper video image is always displayed on the monitor 40, though the two embodiments accomplish this feature in different ways.

A further advantage derived from the latter embodiment 250 relates to the fluoroscope video image displayed on the monitor 40. When the fluoroscope video signal is processed through the photo archiving computer 30, the resulting output signal comprises a reduced fluoroscope image with the remainder of the screen being reserved for graphics, such as the name of the patient, the date of the procedure, and so forth. While such information is useful for later viewing of a stored video image from the photo archiving computer 30 or the video cassette recorder 298, or for identifying a "hard copy" photograph taken by the still photograph unit 304, the information is of no benefit to the physician at the time the procedure is being performed. By routing the fluoroscope video signal directly from the video fluoroscopy control unit 286 to the monitor 40, the apparatus 250 displays a full-screen image from the video fluoroscope 12 on the monitor screen. Should the physician, for some reason, desire to view on the monitor 40 a video image as processed by the photo archiving computer 30, he can select the RGB input on the video monitor, which will display the processed signal from the photo archiving computer arriving via signal path 306.

In actual practice the embodiments 50, 250 may also include an image processor (not shown), a device which would normally be interposed along the signal path 24 between the endoscope 22 and the photo archiving computer 30. An image processor is another electronic device which processes the video signal output from the endoscope 22 and adds rudimentary graphics to the image to identify, for example, the name of the patient and the date of the operation. It will be understood that such a component is redundant given the image processing capabilities of the photo archiving computer 30, and that the video signal is essentially passed through the image processor without being processed to any significant degree. Since the image processor is not necessary to the functioning of the embodiments 50, 250, it has been eliminated for purposes of clarity.

While the foregoing embodiments are disclosed with respect to an apparatus for interfacing with the Olympus Image Manager, it will be appreciated that the device can easily be adapted to other types of photo archiving computers which employ keyboard commands to select from between RGB and NTSC modes of operation. Adapting the apparatus for use with such other types of photo archiving computers may require that coding for a different keystroke sequence be programmed into the keyboard interface 66.

Finally, it will be understood that the preferred embodiment has been disclosed by way of example, and that other modifications may occur to those skilled in the art without departing from the scope and spirit of the appended claims.

What is claimed is:

1. An apparatus comprising:

a first video apparatus generating a video output signal in a first video format;

a second video apparatus generating a video output signal in a second video format which is incompatible with said first video format;

a video component capable of operating in either a first video mode capable of receiving and processing a video signal in said first video format, or a second video mode capable of receiving and processing a video signal in said second video format, said video output signal from said first video apparatus and said second video output signal from said second video apparatus being input into said video component;

a data input device operatively associated with said video component, said video component being responsive to a predetermined signal from said data input device for selecting from between said first video mode and said second video mode for operation;

a switch for selectively actuating and deactuating said first video apparatus, and means for detecting operation of said switch to actuate said first video apparatus and for sending said predetermined signal to said video component to select said first video mode for operation.

2. The apparatus of claim 1, further comprising means for detecting actuation of said switch to deactuate said first video apparatus and for sending said predetermined signal to said video component to select said second video mode for operation.

3. The apparatus of claim 1, wherein said switch comprises a footswitch.

4. The apparatus of claim 1, wherein said first video apparatus comprises a video fluoroscope including an X-ray generator, and wherein said switch for selectively actuating and deactuating said first video component comprises a switch for selectively actuating and deactuating said X-ray generator.

5. The apparatus of claim 1, wherein said second video apparatus comprises an endoscope.

6. The apparatus of claim 1, wherein said video component comprises an apparatus for recording and storing still video images on an archival medium.

7. The apparatus of claim 1, wherein said data input device comprises a keyboard, and wherein said predetermined signal from said data input device comprises a signal corresponding to a predetermined keystroke sequence on said keyboard.

8. The apparatus of claim 1, wherein one of said first and second video formats comprises an NTSC video format and the other of said first and second video formats comprises an RGB video format.

9. An apparatus comprising:

a video fluoroscope generating a video output signal in a first video format;

an endoscope generating a video output signal in a second video format which is incompatible with said first video format;

an X-ray generator operatively associated with said video fluoroscope;

a switch selectively operative to actuate and to deactuate said X-ray generator;

a photo archiving computer component for recording and storing still video images on an archival medium, said photo archiving computer being capable of operating in either a first mode capable of receiving and processing a video signal in said first video format, or a second video mode capable of receiving and processing a video signal in said second video format;

a data input device associated with said photo archiving computer component, said photo archiving computer component normally being responsive to a predetermined signal from said data input device for selecting from between said first video mode and said second video mode for operation;

said video output signal from said video fluoroscope and said video output signal from said endoscope being input into said photo archiving computer component for recording and storing still video images on an archival medium; and means for detecting operation of said switch and for sending said predetermined signal to said photo archiving computer component to select from between said first video mode and said second video mode for operation.

10. The apparatus of claim 9, wherein said means for detecting operation of said switch and for sending said predetermined signal to said photo archiving computer component to select from between said first video mode and said second video mode for operation comprises means for detecting operation of said switch to actuate said X-ray generator and for sending said predetermined signal to said photo archiving computer component to select said first video mode for operation.

11. The apparatus of claim 9, wherein said means for detecting operation of said switch and for sending said predetermined signal to said photo archiving computer component to select from between said first video mode and said second video mode for operation comprises means for detecting operation of said switch to deactuate said X-ray generator and for sending said predetermined signal to said photo archiving computer component to select said second video mode for operation.

12. The apparatus of claim 9 wherein said switch selectively operative to actuate said X-ray generator comprises a footswitch.

13. The apparatus of claim 9, wherein said data input device comprises a keyboard, and wherein said predetermined signal comprises a signal corresponding to a predetermined keystroke sequence on said keyboard.

14. The apparatus of claim 9, wherein one of said first and second video formats comprises an NTSC video format and the other of said first and second video formats comprises an RGB video format.

15. An apparatus for use with in combination a video fluoroscope generating a video output signal in a first video format, an endoscope generating a video output signal in a second video format which is incompatible with said first video format, an X-ray generator operatively associated with said video fluoroscope, a switch selectively operative to actuate said X-ray generator, a photo archiving computer component for recording and storing still video images on an archival medium, said photo archiving computer being capable of operating in either a first mode capable of receiving and processing a video signal in said first video format, or a second video mode capable of receiving and processing a video signal in said second video format, said photo archiving computer component normally being responsive to a predetermined signal from a data input device associated therewith for selecting from between said first video mode and said second video mode for operation, said video output signal from said endoscope and said video output signal from said video fluoroscope being input into said photo archiving computer component for recording and storing still video images on an archival medium, said apparatus comprising:

detection means operatively associated with said switch for detecting actuation of said switch to actuate said X-ray generator; and signal generation means responsive to said detection means detecting actuation of said switch to actuate said X-ray generator for sending said predetermined signal to said photo archiving computer component to select said first video mode for operation.

16. The apparatus of claim 15, further comprising means for detecting actuation of said switch to deactuate said X-ray generator and for sending said predetermined signal to said photo archiving computer component to select said second video mode for operation.

17. The apparatus of claim 15, wherein said data input device associated with said photo archiving computer component comprises a keyboard, wherein said predetermined signal comprises a signal corresponding to a predetermined keystroke sequence, and wherein said means for sending said predetermined signal to said photo archiving computer comprises means for sending said signal corresponding to said predetermined keystroke sequence to said photo archiving computer.

* * * * *